United States Patent [19]
Janoff et al.

[11] Patent Number: 5,882,678
[45] Date of Patent: Mar. 16, 1999

[54] INTERDIGITATION-FUSION LIPOSOMES CONTAINING ARACHIDONIC ACID METABOLITES

[75] Inventors: Andrew S. Janoff, Yardley, Pa.; Sharma R. Minchey, Monmouth Junction, N.J.

[73] Assignee: The Liposome Co, Inc., Princeton, N.J.

[21] Appl. No.: 339,964

[22] Filed: Nov. 15, 1994

Related U.S. Application Data

[63] Continuation-in-part of Ser. No. 153,176, Nov. 16, 1993, abandoned, which is a continuation-in-part of Ser. No. 315,988, Sep. 30, 1994, which is a continuation-in-part of Ser. No. 136,470, Oct. 13, 1993, abandoned, which is a continuation-in-part of Ser. No. 66,539, May 24, 1993, abandoned, which is a continuation-in-part of Ser. No. 961,277, Oct. 14, 1992, abandoned, which is a continuation-in-part of Ser. No. 664,576, Mar. 5, 1991, abandoned, which is a continuation-in-part of Ser. No. 464,528, Jan. 12, 1990, abandoned.

[51] Int. Cl.$^6$ ..................................................... A61K 9/127
[52] U.S. Cl. .......................... 424/450; 514/573; 514/825; 514/866
[58] Field of Search ............................ 424/450; 514/573, 514/825, 866

[56] References Cited

U.S. PATENT DOCUMENTS

| | | | |
|---|---|---|---|
| 4,229,360 | 10/1980 | Schneider et al. | 260/403 |
| 4,493,847 | 1/1985 | Mizishuma et al. | 424/317 |
| 4,684,633 | 8/1987 | Imagawa et al. | 514/78 |
| 4,820,732 | 4/1989 | Shell et al. | 514/573 |
| 4,837,028 | 6/1989 | Allen et al. | 424/450 |
| 4,880,635 | 11/1989 | Janoff et al. | 424/450 |
| 4,920,016 | 4/1990 | Allen et al. | 424/450 |
| 4,955,878 | 9/1990 | See et al. | 604/181 |
| 5,013,556 | 5/1991 | Woodle et al. | 424/450 |
| 5,077,056 | 12/1991 | Bally et al. | 424/450 |
| 5,262,168 | 11/1993 | Leuk | 424/450 |
| 5,283,122 | 2/1994 | Huang | 428/402.2 |

FOREIGN PATENT DOCUMENTS

| | | | |
|---|---|---|---|
| 0 292 403 | 11/1988 | European Pat. Off. | A61K 9/50 |
| 0 512 916 | 11/1992 | European Pat. Off. | A61K 31/557 |
| 5-139977 | 6/1993 | Japan | A61K 31/557 |
| 91/10422 | 7/1991 | WIPO | A61K 9/133 |
| 9110422 | 7/1991 | WIPO . | |

OTHER PUBLICATIONS

Blume, et al., "Specific targeting with poly(ethylene glycol)–modified liposomes: coupling of homing devices to the ends of the polymeric chains combines effective target binding with long circulation times", Biochem. Biophy. Acta. 1149:180–184, 1993.

Gabizon, et al., "Prolongation of the Circulation Time of Doxorubicin Encapsulated in Liposomes Containing a Polyethylene Glycol–Derivatized Phospholipid: Pharmacokinetic Studies in Rodents and Dogs", Pharm. Res. 10(5):703, 1993.

Goodman and Gilman's The Pharmacological Basis of Therapeutics, Goodman gilman et al., eds. Pergamon Press, New York, 1990, pp. 600–611.

Hoshi, et al., "Prostaglandin $E_1$ Incorporated in Lipid Microspheres in the Treatment of Peripheral Vaculare Diseases and Diabetic Neuropathy", Drugs. Exptl. Clin Res. 12 (8):681, 1986.

(List continued on next page.)

*Primary Examiner*—Gollamudi S. Kishore
*Attorney, Agent, or Firm*—Kenneth B. Rubin

[57] ABSTRACT

This invention provides an interdigitation-fusion liposome comprising an arachidonic acid metabolite, a lipid bilayer comprising a lipid and an aqueous compartment comprising a release-inhibiting buffer. Preferred arachidonic acid metabolites are the prostaglandins, particularly $PGE_1$. The liposomal formulations can be used to treat animals, particularly humans, for diseases, disorders or conditions which can be ameliorated by prostaglandins, e.g., cell activation/adhesion disorders and inflammatory disorders.

18 Claims, 1 Drawing Sheet

OTHER PUBLICATIONS

Mizishuma et al., "A Multicenter Double Blind Controlled Study of Lipo–$PGE_1$, $PGE_1$ Incorporated in Lipid Microspheres, in Peripheral Vascular Disease Secondary to Connective Tissue Disorders", J. Rheumatol. 14:97 (1987).

Park et al., "Some negatively charged phospholipid derivatives prolong the liposome circulation in vivo", Biochim. Biophys Acta. 1108: 257, 1992.

Stedman's Medical Distionary (Illustrated), (24th edition J. V. Basmajian et al., eds.) Williams and Wilkins, Baltimore, MD, 1982, pp. 123–124 and 707–708.

Stryer, Biochemistry (2nd edition), W. H. Freeman and Co. New York 1981, pp. 853–854.

"Adhesion in Disease and Therapy,", (Springer et al., eds.) in: *Leukocyte Adhesion Molecules,* Springer–Verlag, New York, (1990) pp. 85–156.

INTERDIGITATION-FUSION LIPOSOMES CONTAINING ARACHIDONIC ACID METABOLITES

This application is a continuation-in-part of U.S. Ser. No. 08/315,988, filed Sep. 30, 1994, now pending which is a continuation-in-part of U.S. Ser. No. 08/136,470, filed Oct. 13, 1993 and now abandoned, a continuation-in-part of U.S. Ser. No. 08/066,539, filed May 24, 1993 and now abandoned, and a continuation-in-part of U.S. Ser. No. 07/961,277, filed Oct. 14, 1992 and now abandoned. U.S. Ser. No. 07/961,277 is in turn a continuation-in-part of U.S. Ser. No. 07/664,576, filed Mar. 5, 1991 and now abandoned, which-in-turn is a continuation-in-part of U.S. Ser. No. 07/464,528, filed Jan. 12, 1990 and now abandoned. This application is also a continuation-in-part application of U.S. Ser. No. 08/153,176 filed Nov. 16, 1993, which is abandoned. This application is directed to liposomal formulations of arachidonic acid metabolites. The liposomal formulations of this invention can be used therapeutically in diseases, disorders or conditions which can be ameliorated by prostaglandins.

Arachidonic acid, and other twenty carbon "essential" fatty acids having at least three double bonds, can be used to make prostaglandins (for a review, see, e.g., *Goodman and Gilman's The Pharmacological Basis of Therapeutics* (A. Goodman Gilman et al., eds.), Pergamon Press, New York (1990), pp. 600–611); L. Stryer, *Biochemistry* (2nd edition), W. H. Freeman and Co., New York (1981), pp. 853–854)). The various prostaglandins are grouped into several categories (A-I), which are distinguished by varying substituents on the five-carbon ring introduced into the twenty-carbon fatty acid precursor during prostaglandin synthesis. These groups can be further subdivided based upon the number, and position, of double bonds in the prostaglandins' carbon chains.

Prostaglandins are believed to act on their target cells by way of cellular surface receptors; these receptors are believed to be coupled to second messenger systems by which prostaglandin action is mediated. Prostaglandins can have a broad spectrum of biological activities. They can act on smooth vascular muscle and thereby be potent vasodilators; prostaglandins can also affect the functioning of blood cells, particularly neutrophils and platelets. Uterine contractions can be affected by prostaglandin action, which can also affect renal, central nervous system and afferent nerve function. Various endocrine tissues can respond to prostaglandins. Furthermore, prostaglandins can modulate inflammatory conditions in animals.

Enzymes in the body can rapidly deactivate prostaglandins. This typically necessitates frequent administrations of high doses of the compounds to maintain therapeutically effective levels in the serum, thereby increasing the expense of prostaglandin treatment and leading to the possibility of unwanted side effects. Furthermore, as prostaglandin deactivation occurs primarily as blood passes through the lungs, the compounds are generally administered intra-arterially.

Liposomal formulations can prolong the circulatory half-lives of arachidonic acid metabolites, e.g., prostaglandins, and can help avoid their deactivation in the lungs. Accordingly, such liposomal formulations can provide therapeutically useful alternatives for prostaglandin treatment. Mizishuma et al. (J. Rheumatol. 14:97 (1987)) and Hoshi et al. (Drugs. Exptl. Clin. Res. 12(8):681 (1986)) describe lipid microspheres containing prostaglandin E1 ($PGE_1$). However, as disclosed in Mizishuma et al. (U.S. Pat. No. 4,493,847) and Imagawa et al. (U.S. Pat. No. 4,684,633), these "microspheres" are actually prostaglandin-containing fat emulsions, which are not liposomes, and have neither the same properties, nor the same advantages, as the liposomal prostaglandins provided herein. Shell and See (U.S. Pat. Nos. 4,820,732 and 4,955,878) disclose treatments for reducing dysfunction during angioplasty procedures which involve administering prostaglandin-containing compositions to patients. These compositions also contain a carrier. However, the liquid carriers disclosed, e.g., dehydrated alcohols and saline solutions, generally cannot provide sustained release of a prostaglandin. The fat-laden microsphere carriers disclosed are taught to be at least as large as a red blood cell, i.e, at least 7 microns in diameter, and can be much larger. Administration of particles of such large size to animals can cause difficulties because the microspheres can become stuck in, and clog, small blood vessels, e.g., lung capillaries.

Liposomes are self-assembling structures comprising one or more bilayers of amphipathic lipid molecules, each of which encloses an internal aqueous volume. Unilamellar liposomes have a single lipid bilayer. Multilamellar liposomes have two or more lipid bilayers. Interdigitation-fusion vesicles (IFVs) can be unilamellar or multilamellar, but are typically predominantly unilamellar. Individual IFVs can also be both unilamellar and multilamellar.

The lipid bilayers of IFVs comprise interdigitated lipids, i.e., the acyl chains of the lipids in each monolayer of a bilayer cross the bilayer midplane and interpenetrate into the opposing monolayer, where they can interact with the acyl chains. IFVs can be produced by inducing the fusion of other liposomes (see Boni et al., PCT Publication No. WO 91/10422 (Jul. 25, 1991) and Boni et al., U.S. Ser. Nos. 07/961,277, abandoned, 08/066,539, abandoned, and 08/136,470, abandoned, filed Oct. 14, 1992, May 24, 1993, and Oct. 13, 1993, respectively; the contents of these U.S. patent applications are incorporated herein by reference).

Liposomes can be loaded with bioactive agents passively, i.e., by solubilizing the molecule in the medium in which the liposomes are formed, in the case of water-soluble agents, or adding lipid-soluble agents to the lipid solutions from which the liposomes are made. Ionizable bioactive agents can also be loaded into liposomes actively, e.g., by establishing an electrochemical potential gradient across the liposomal membrane and then adding the agent to the medium external to the liposome (see Bally et al., U.S. Pat. No. 5,077,056, the contents of which are incorporated herein by reference).

Liposomal formulations of drugs can have an enhanced therapeutic index by reducing the drug's toxicity, increasing its efficacy, or both. Furthermore, liposomes, like other particulate matter in the circulation, are typically taken up by phagocytic cells of the reticuloendothelial system in tissues having sinusoidal capillaries, and are thereby often directed to sites of intracellular infections.

Maximizing the efficiency with which drugs are entrapped in liposomes can minimize the lipid load presented to treated subjects and can also minimize the waste of valuable drug products. The release of compounds which tend to leak from liposomes should also be inhibited to derive the maximum benefit from their encapsulation. Furthermore, the provision of liposomal formulations which can be stably stored will increase the therapeutic benefits derived therefrom.

This invention provides liposomal formulations which are directed to these concerns. These formulations can enhance the therapeutic index of arachidonic acid metabolites, in comparison to their administration in the free (unentrapped) form.

The liposomal arachidonic acid metabolite formulations of this invention are useful in ameliorating or preventing diseases, disorders or conditions which can be treated with a prostaglandin. Disorders which can be treated with these formulations include cell activation/adhesion disorders and inflammatory disorders. Cell activation/adhesion disorders are characterized by abnormal activation of cells in the blood; the activated cells can adhere to each other, or to activated cells in surrounding vascular endothelium. Such adhesions can lead to the blockage of small blood vessels, e.g., lung capillaries, consequent stoppage of blood flow, and subsequent damage to surrounding tissue. Amongst the cell activation/adhesion disorders to which the present invention is directed are reperfusion injuries, septic shock, myocardial infarction, adult respiratory distress syndrome (ARDS), rheumatoid and systemic vasculitis, lupus, post-traumatic shock, burn injuries and restenosis after angioplasty.

Prostaglandin treatment can reduce the damage exhibited in animals afflicted with such disorders. The same cells which become activated undergo subsequent intracellular adhesion, can also have surface prostaglandin receptors. Without intending in any way to be limited by theory, it is believed that when prostaglandins bind to these cellular prostaglandin receptors, they can deactivate the surface receptors which, when activated, appear to be responsible for the elevated levels of intercellular adhesion.

Inflammation is a process of cytological and histological reactions occurring in affected blood vessels, and surrounding tissues, in response to an injury (see, e.g., *Stedman's Medical Dictionary (Illustrated)* (24th edition, J. V. Basmajian et al., eds.), Williams and Wilkins, Baltimore, Md. (1982), pp. 707–708). Inflammatory responses to injuries include local reactions and resulting morphological changes, destruction or removal of injurious materials and activation of repair mechanisms. Thus, inflammation can be part of the process by which animals heal themselves. However, inflammation, such as when it occurs in response to abnormal physiological stimuli, can itself cause problems in the body. Joints, for example, become inflamed in arthritic conditions such as gout, rheumatoid arthritis and Lyme disease (see, e.g., *Stedman's Medical Dictionary (Illustrated)*, supra at pages 123–124). These states may be characterized by the extravasation of cells, i.e, the egress of cells from the circulation into the inflamed area. Agents, such as arachidonic acid metabolites, e.g., prostaglandins, which can inhibit such extravasation, or which can otherwise inhibit inflammatory responses to abnormal physiological stimuli, can be used to treat inflammatory disorders.

The contents of U.S. Ser. No. 07/821,648, filed Jan. 16, 1992, which is directed to liposomal arachidonic acid metabolite compositions, are incorporated by reference herein. The contents of U.S. Ser. No. (08/147,898) filed Nov. 4, 1993, which is a continuation of U.S. Ser. No. 07/876,200, filed Apr. 30, 1992, and which is directed to methods of treating cell activation/adhesion disorders, are also incorporated herein by reference.

SUMMARY OF THE INVENTION

This invention provides an interdigitation-fusion liposome comprising an arachidonic acid metabolite, a saturated acyl-chain lipid and a compartment comprising a release-inhibiting aqueous buffer. Preferably, the arachidonic acid metabolite is a prostaglandin. More preferably, the prostaglandin is a prostaglandin of the E series or a prostaglandin of the I series. Most preferably, the prostaglandin is prostaglandin $E_1$. Preferably, the release-inhibiting aqueous buffer is a citric acid buffer; most preferably, a citric acid buffer having a pH of about 4.5. Preferably, the saturated-acyl chain lipid is distearoyl phosphatidylcholine or dipalmitoyl phosphatidylcholine.

Desirably, the interdigitation-fusion liposome comprises a drying protectant. Preferably, the drying protectant is a sugar. More preferably, the sugar is maltose, dextrose, galactose, lactose, raffinose or trehalose. Most preferably, the sugar is maltose.

Accordingly, in preferred embodiments of the invention, the interdigitation-fusion liposome comprises a saturated-acyl chain lipid, an aqueous compartment comprising a citric acid buffer having a pH of about 4.5 and prostaglandin E1, wherein the saturated-acyl chain lipid is dipalmitoyl phosphatidylcholine or distearoyl phosphatidylcholine. More preferably, this IF liposome comprises a a drying protectant.

The IF liposome of this invention can have a lipid bilayer which comprises a headgroup-modified lipid. The liposome can comprise an additional bioactive agent; the liposome can also be dehydrated. The dehydrated liposome can comprise a drying protectant.

Also provided herein is a composition comprising a pharmaceutically acceptable carrier and the interdigitation-fusion liposome.

Further provided herein is a two-component system which comprises:(a) a dehydrated interdigitation-fusion liposome comprising an arachidonic acid metabolite and a lipid bilayer comprising a saturated-acyl chain lipid; and an aqueous solution, wherein the dehydrated interdigitation-fusion liposome and the aqueous solution are combined so as to rehydrate the dehydrated liposome.

Still further provided is a method of administering an arachidonic acid metabolite to an animal which comprises administering to the animal an interdigitation-fusion liposome comprising the metabolite, a lipid bilayer comprising a saturated acyl chain lipid and a compartment comprising a release-inhibiting aqueous buffer. The metabolite is preferably prostaglandin E1 the animal is preferably a human, and the administration preferably comprises intravenous administration.

The method of this invention can be used to treat animals afflicted with a disorder characterized by cell activation and adhesion, inflammation or toxemia, wherein an amount of the composition comprising an anti-disorder effective amount of the arachidonic acid metabolite is administered to the animal. The disorder treated, which can be any disorder amenable to treatment with an arachiodonic acid metabolite, is typically a vaso-occlusive disorder, an arthritic disorder or an autoimmune disorder. Generally, the disorder treated can comprise vasculitis, reperfusion injury, post-traumatic shock, myocardial infarction, rheumatoid arthritis, gout, systemic lupus erythematosus, juvenile diabetes, multiple sclerosis, Hashimoto's thyroiditis, septic shock, systemic inflammatory response syndrome, adult respiratory distress syndrome, post-operative complications, myasthenia gravis, burn injury or restenosis after angioplasty. Preferably, the disorder treated is adult respiratory distress syndrome (ARDS) or systemic inflammatory response syndrome (SIRS).

Typically, the effective amount of the metabolite is at least about $10^{-12}$ g of the metabolite per kg of body weight of the animal. Generally, the effective amount of the metabolite is from about $10^{-12}$ g of the metabolite per kg of body weight of the animal to about $10^{-3}$ g per kg of body weight. Preferably, the effective amount of the metabolite is from about $10^{-8}$ of the metabolite per kg of body weight of the animal to about $10^{-4}$ g per kg of body weight. More preferably, the anti-cell activation and adhesion effective amount of the arachidonic acid metabolite is about $10^{-6}$ g of the metabolite per kg of body weight of the animal.

Furthermore, the method of this invention can comprise administering an additional bioactive agent to the animal.

DETAILED DESCRIPTION

Figure 1:
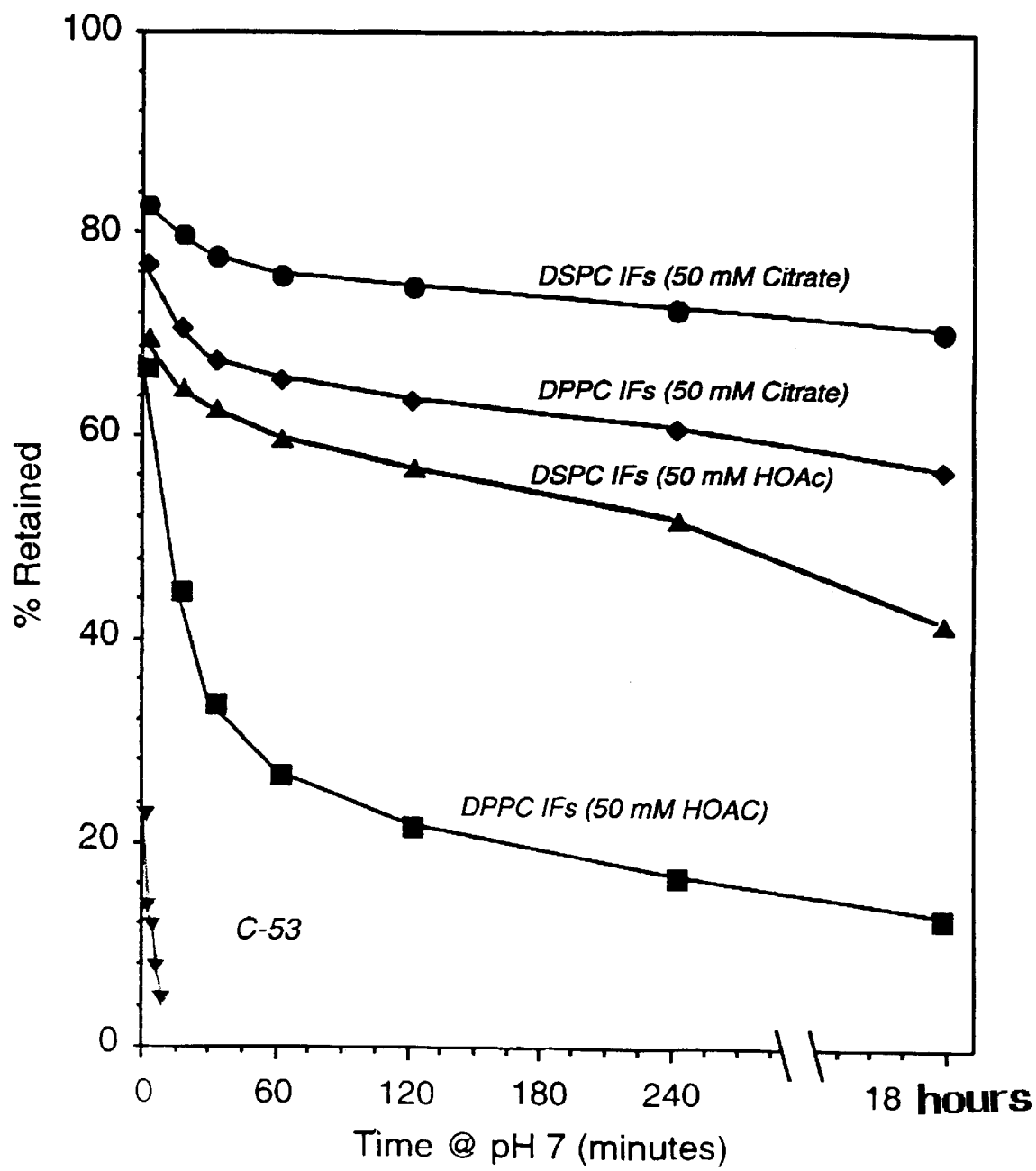
FIG. 1. Release of PGE, From Interdigitation-Fusion Liposomes (IFVs). IFVs prepared in accordance with procedures described below, were incubated in a buffer of about pH 7 for the indicated time (x-axis, minutes), following which the percent prostaglandin retained in the pellet (y-axis) was determined. Filled circles: IFVS containing distearoyl phosphatidylcholine (DSPC; 50 mM citrate buffer); filled diamonds: dipalmitoyl phosphatidylcholine-containing IFVs (DPPC; 50 mM citrate buffer); filled triangles: DSPC-IFVs (50 mM acetate buffer); filled squares: DPPC-IFVs (50 mM acetate); filled triangles, inverted: C-53.

This invention provides an interdigitation-fusion liposome which comprises an arachidonic acid metabolite, a lipid bilayer comprising a saturated-acyl chain lipid and a compartment comprising a release-inhibiting aqueous buffer. Liposomes are self-assembling structures comprising one or more bilayers of amphipathic lipid molecules, each of which encloses an internal aqueous volume. The amphipathic lipid molecules which make up lipid bilayers comprise a polar (hydrophilic) headgroup region covalently linked to one or two non-polar (hydrophobic) acyl chains. The energetically unfavorable contact between the hydrophobic acyl chains and the aqueous medium causes the lipid molecules to rearrange such that the polar headgroups are oriented towards the aqueous medium while the acyl chains reorient towards the interior of the bilayer. The net result is an energetically stable structure in which the acyl chains are effectively shielded from coming into contact with the aqueous medium.

Interdigitation-fusion liposomes (IFVs) can be unilamellar or multilamellar, but are generally predominantly multilamellar; individual IFVs can also be both unilamellar and multilamellar. The lipid bilayers of IFVs comprise interdigitated lipids and are produced by inducing the fusion of other lipid vesicles (see Boni et al., PCT Publication No. WO 91/10422 (Jul. 25, 1991) and Boni et al., U.S. Ser. Nos. 07/961,277, 08/066,539 and 08/136,470, which is a continuation-in-part of U.S. Ser. Nos. 07/961,277 and 08/066,539, filed Oct. 14, 1992, May 24, 1993 and Oct. 13, 1993, respectively; the contents of these U.S. patent applications are incorporated herein by reference). Interdigitation, which renders the lipid bilayer less susceptible to perturbation during liposome formation, can be utilized to prepare liposomes with high captured volumes.

"Interdigitation" and "interdigitated" are used herein to denote lipid bilayers in which acyl chains of lipids in each monolayer cross the bilayer midplane and interpenetrate into the opposing monolayer. Lipids may be fully interdigitated; "full interdigitation" describes lipid bilayers in which acyl chains in each monolayer of the bilayer span the entire width of the bilayer, i.e., where there are four acyl chains per headgroup surface area. Lipids with asymmetric acyl chains, i.e., lipids having acyl chains of uneven length, can also undergo mixed or partial interdigitation.

The production of interdigitation-fusion liposomes involves the incubation of sized liposomes in the presence of an amount of an inducer effective to fuse the liposomes. Sized liposomes can fuse into lipid sheets (gels) at certain concentrations of inducer in order to relieve bilayer strain imposed by their small radius of curvature. Any of the methods available in the art for producing a population of sized liposomes from other liposomes, such as sonication, extrusion or homogenization may be utilized. After the formation of sized liposomes, the solute, preferably a bioactive agent, that is to be encapsulated is generally mixed in the aqueous solvent. The amount of inducer, e.g., short-chain organic compounds such as ethanol, hydrostatic pressure and self-inducing lipids, used will depend, for example, upon the type of inducer used, and the nature of the sized liposome utilized.

Liposomes can be loaded with bioactive agents passively, i.e., by solubilizing the molecule in the medium in which the liposomes are formed, in the case of water-soluble agents, or adding lipid-soluble agents to the lipid solutions from which the liposomes are made. Ionizable bioactive agents can also be loaded into liposomes actively, e.g., by establishing an electrochemical potential gradient across the liposomal membrane and then adding the ionizable agent to the medium external to the liposome (see Bally et al., U.S. Pat. No. 5,077,056, the contents of which are incorporated herein by reference).

"Arachidonic acid metabolites" are prostaglandins, or compounds which can be converted to prostaglandins, e.g., artificially or in the body of an animal. Prostaglandins are a group of twenty-carbon fatty acids containing a five-carbon ring, plus seven- and eight-carbon chains, that are made from other twenty-carbon fatty acids having at least three double bonds, i.e., twenty-carbon essential fatty acids (e.g., 8,11,14-eicosatrienoic acid, 5,8,11,14-eicosatetraenoic acid or 5,8,11,14,17-eicosapentanoic acid; see, e.g., *Goodman and Gilman's The Pharmacological Basis of Therapeutics*, supra). Arachidonic acid is the most abundant of these twenty-carbon prostaglandin precursors in humans.

The twenty-carbon essential fatty acid prostaglandin precursors, intermediates formed during prostaglandin synthesis, e.g., prostanoic acid, and structural analogs which can be converted to these compounds, are "arachidonic acid metabolites." "Prostaglandin-related compounds," e.g., leukotrienes, thromboxanes, lipoxins and prostacyclins, include those compounds which are functionally related to prostaglandins and which can also be derived from the twenty carbon essential fatty acid prostaglandin precursors; prostaglandins and prostaglandin-related compounds can be referred to as eicosanoids. The prostaglandins and the prostaglandin-related compounds, as well as structural analogs which can be converted to such compounds, are also "arachidonic acid metabolites."

Prostaglandins are the preferred arachidonic acid metabolites. The various prostaglandins are classified in several major groups (A-I) according to the arrangement of substituents on the five-carbon rings; these groups can be further subdivided based on the number, and position, of double bonds in the prostaglandins' carbon chains. Preferred prostaglandins are the E series or I series prostaglandins; most preferably, the prostaglandin is $PGE_1$.

Prostaglandins are rapidly and efficiently catabolized and inactivated in the body. The compounds lose most of their biological activity as a result of reactions catalyzed by a series of prostaglandin-specific enzymes; the next step in the inactivation process is carried out by enzymes of the fatty acid oxidation pathways. The prostaglandins can have a broad spectrum of biological activities. E series prostaglandins, for example, can affect smooth vascular muscle, e.g., arterioles, precapillaries, sphincters and post-capillary venules, and can be potent vasodilators. $PGD_2$, $PGF_{alpha}$ and $PGI_2$ can also have vasodilative effects. Prostaglandins, and related derivatives, can affect the functioning of blood cells, particularly neutrophils and platelets. $PGI_2$, for example, can inhibit platelet aggregation at concentrations as low as 1 nM (see Goodman Gilman's The Pharmacological Basis of Therapeutics, supra). Uterine contractions can be affected by PGE, PGF and PGI action. Prostaglandins can also affect renal, central nervous system and afferent nerve function. Various endocrine tissues typically respond to prostaglandins. Furthermore, prostaglandins can modulate inflammatory responses.

Prostaglandins are believed to act by binding to surface receptors on their targets. These receptors are believed to be coupled to second messenger systems through which the effects of prostaglandins on target cells are mediated.

The rapid enzymatic deactivation which prostaglandins can undergo in the body frequently necessitates recurring administrations of high doses of prostaglandins in order to maintain therapeutically effective levels in the serum. Such a therapeutic regimen increases the expense of prostaglandin treatment and can lead to unwanted side effects; elevated $PGE_1$ levels, for example, can induce hypotension, tachycardia and diarrhea. Furthermore, as prostaglandin deactivation occurs primarily in the lungs, intra-arterial administration is generally required.

The interdigitation-fusion liposomes of this invention comprises a lipid bilayer comprising a saturated-acyl chain lipid, i.e., a lipid with acyl chains without double bonds between the carbon atoms. Saturated acyl chain lipids increase the strength of prostaglandin-lipid interactions, and thereby inhibit release of prostaglandins from liposomes. Such lipids may also be referred to as "release-inhibiting lipids." Release-inhibiting lipids tend to increase the strength of prostaglandin-lipid interactions by, for example, making lipid bilayers less permeable to water and other small molecules, e.g., by increasing Van der Waals, dipole-dipole and other interactions between acyl chains and hence, inducing acyl chains to pack more closely together in the lipid bilayer. The number of double bonds in the bilayer's acyl chains can affect the chains' arrangement with respect to each other in the bilayer. The lower the number of double bonds, the more closely acyl chains are likely to pack together, and hence, are more likely to present a barrier to molecules transiting the bilayer. Presently, the preferred saturated-acyl chain, release-inhibiting lipids are dipalmitoyl phosphatidylcholine (DPPC) and distearoyl phosphatidylcholine (DSPC). However, other saturated-acyl chian chain lipids can also be used.

The factors which tend to enhance prostaglandin-lipid associations can also tend to enhance the association of prostaglandins with lipids during liposome formation and hence, the percentage of available prostaglandin associated with the liposomes. Prostaglandin-liposome "association" referred to herein means prostaglandin-lipid bilayer interactions, physically or chemically, or entrapment of a prostaglandin in the aqueous compartment of a liposome. Preferred associations comprise interactions prostaglandin-lipid bilayer interactions.

Aqueous buffers in liposomes can also inhibit or prevent release of a prostaglandin associated with a liposome. Such aqueous buffers can be referred to as "release-inhibiting buffers." Aqueous buffers, one or more of whose components tends to increase the strength of prostaglandin-lipid associations, are preferred release-inhibiting buffers herein. Characteristics of preferred release-inhibiting buffers include, but are not limited to the ability to establish electrostatic repulsions with prostaglandins and thereby enhance prostaglandin-lipid interactions. Furthermore, buffers with a higher buffering capacity, and hence a greater ability to maintain the desired pH, will be better release-inhibiting buffers. Preferred release-inhibiting buffers are citric acid buffers, e.g., those citric acid buffers having a pH of about 4.5.

The interdigitation-fusion liposome of this invention can comprise a drying protectant, which is preferably a sugar, e.g., maltose, dextrose, galactose, lactose, raffinose or trehalose. Preferably, the sugar is maltose. The drying protectant can be used when dehydrating the liposomes. Without intending to be bound by theory, it is believed that the drying protectant maintains the size and integrity of the liposomes through the dehydration/rehydration process.

Accordingly, the interdigitation-fusion liposome of this invention preferably comprises $PGE_1$, an aqueous compartment comprising a citric acid buffer having a pH of about 4.5, and a lipid bilayer comprising DPPC or DSPC. The preferred interdigitation-fusion liposome can comprise a drying protectant, e.g., maltose.

The interdigitation-fusion liposome of this invention can comprise an additional bioactive agent, such as, another arachidonic acid metabolite, e.g., a prostaglandin. "Bioactive agent" as used herein denotes any compound or composition of matter having biological activity in animals, e.g., humans. Bioactive agents include, but are not limited to: antiviral, antibacterial, antifungal, antiparasitic, antimetabolic, antiglaucomic, anti-inflammatory or antineoplastic compounds, sterols, carbohydrates, amino acids, peptides, proteins, immunoglobulins, immunomodulators, dyes, toxins, enzymes, hormones, neurotransmitters, glycoproteins, radiolabels, radiopaque compounds, fluorescent compounds, cell receptor proteins, cell receptor ligands, mydriatic compounds, bronchodilators, local anesthetics, growth promoting agents, regenerative agents and the like. The second bioactive agont may comprise an additional, or second, arachidonic acid metabolite, e.g., another prostaglandin.

The interdigitation-fusion liposome of this invention can further comprise a headgroup-modified lipid. Liposomes are cleared from an animal's body by way of its reticuloendothelial system (RES) which consists of fixed and circulating macrophages. Avoiding RES clearance allows liposomes to remain in the circulation longer, meaning that less of the drug need be administered to achieve desired serum levels. Enhanced circulation times can also allow targeting of liposomes to non-RES containing tissues. Liposomal surfaces become coated with serum proteins when administered to animals. Rates of clearance by the RES can be related to the rate and level of such protein coating; accordingly, clearance can be inhibited by modifying the outer surface of liposomes such that binding of serum proteins is generally inhibited. This can be accomplished by minimizing or shielding negative surface charges, which can promote protein binding, or by otherwise presenting a steric hindrance to the binding of serum proteins.

Effective surface modification, that is, alterations to the outer surfaces of liposomes which result in inhibition of RES uptake, can be accomplished by incorporating headgroup-modified lipids into liposomal bilayers. "Headgroup-modified lipids" as used herein are amphipathic lipids whose polar headgroups have been derivatized by attachment thereto of a chemical moiety, e.g., polyethylene glycol, a polyalkyl ether, a ganglioside, an organic dicarboxylic acid, e.g., glutaric acid, or the like, which can inhibit the binding of serum proteins to liposomes such that the pharmacokinetic behavior of the vesicles in the circulatory systems of animals is altered (see, e.g., Blume et al., Biochim. Biophys. Acta. 1149:180 (1993); Gabizon et al., Pharm. Res. 10(5):703 (1993); Park et al. Biochim. Biophys Acta. 1108: 257 (1992); Woodle et al., U.S. Pat. No. 5,013, 556; Allen et al., U.S. Pat. Nos. 4,837,028 and 4,920,016; the contents of these disclosures are incorporated herein by reference). The liposome provided by this invention can further comprise such a headgroup-modified lipid. The amount of the headgroup-modified lipid incorporated into the liposome depends upon a number of factors well known to the ordinarily skilled artisan, or within his purview to determine without undue experimentation. These include, but are not limited to: the type of lipid and the type of headgroup modification; the type and size of the liposome; and the intended therapeutic use of the liposomal formulation. Typically, the concentration of the headgroup-modified lipid in the liposome is at least about five mole percent, desirably, about ten mole percent.

Also provided herein is a dehydrated interdigitation-fusion liposome comprising an arachidonic acid metabolite and a lipid bilayer comprising a saturated-acyl chain lipid. Liposomal dehydration enables liposomes to be stored for extended periods of time; they can then be reconstituted on an as-needed basis for administration to subjects. Liposomes can be dehydrated, with freezing, using standard freeze-drying equipment, or its equivalents. Lyophilization is preferably carried out after incorporating one or more drying protectants, preferably, protective sugars, into liposome preparations in accordance with the procedures of Schneider et al. (U.S. Pat. No. 4,229,360) and Janoff et al., (U.S. Pat. No. 4,880,635 (PCT Publication No. WO 86/01103 (Feb. 27, 1986))), the contents of which are incorporated herein by reference. The protective sugar, e.g., maltose, sucrose, dextrose, raffinose, trehalose, lactose or galactose, but preferably maltose, can be omitted if the dehydration is conducted without freezing and sufficient water is left remaining in the liposomal preparation to maintain the integrity of a substantial portion of the liposomal bilayers through the dehydration-rehydration process. The dehydrated interdigitation-fusion liposome of this invention can comprise a drying protectant, e.g., maltose.

This invention provides a two-component system which comprises a dehydrated interdigitation-fusion liposome comprising an arachidonic acid metabolite and a lipid bilayer comprising a saturated-acyl chain lipid, and an aqueous solution. The aqueous solution and the dehydrated interdigitation-fusion liposome are combined so as to rehydrate or reconstitute the dehydrated liposome. The aqueous solution can be a number of solutions including the pharmaceutically acceptable carriers, e.g., aqueous buffered solutions, disclosed herein. The components can be provided in vials or other packaging in which it is convenient to store and combine the components.

Further provided is a pharmaceutical composition comprising a pharmaceutically acceptable carrier and the interdigitation-fusion liposome of this invention, i.e., an interdigitation-fusion liposome comprising an arachidonic acid metabolite, a lipid bilayer comprising a saturated-acyl chain lipid and an aqueous compartment comprising a release-inhibiting buffer. Preferably, the arachidonic acid metabolite is $PGE_1$, the release-inhibiting buffer is a citric acid buffer having a pH of about 4.5, and the saturated-acyl chain lipid is DPPC or DSPC. "Pharmaceutically acceptable carrier" as used herein means any of the standard carriers, diluents, excipients and the like generally intended for use in connection with the administration of bioactive agents to animals, particularly humans. Such carriers are well known in the art and are generally chosen with regards to a number of factors, such as the particular drug being used and the intended route of administration, which are well understood by the ordinarily skilled artisan, or are within his purview to determine without undue experimentation. Suitable carriers include, but are not limited to, salt solutions such as physiological saline, aqueous dextrose solutions, e.g., D5W, and the like. The pharmaceutical composition can further comprise auxiliary agents such as preservatives, anti-oxidants and the like in amounts, and for reasons, well known to the ordinarily skilled artisan.

This invention provides a method of administering an arachidonic acid metabolite to an animal, preferably, a human. The method comprises administering to the animal a composition comprising a pharmaceutically acceptable carrier and the lioposomal formulations of this invention. Preferably, the administration comprises intravenous administration.

The liposomal formulations of this invention can be used to prevent or ameliorate diseases, disorders or conditions susceptible to prostaglandin treatment, such as those disorders characterized by cell activation and adhesion, inflammation or toxemia, by administering to the animal an anti-disorder effective amount of an arachidonic acid metabolite associated with an IF liposome. Generally, the disorder comprises vaso-occlusive, arthritic and autoimmune disorders, such as vasculitis, post-traumatic shock, myocardial infarction, rheumatoid arthritis, gout, systemic lupus erythematosus, juvenile diabetes, multiple sclerosis, Hashimoto's thyroiditis, septic shock, systemic inflammatory response syndrome, adult respiratory distress syndrome, post-operative complications, myasthenia gravis, burn injury or restenosis after angioplasty. Preferably, the disorder treated is adult respiratory distress syndrome (ARDS) or systemic inflammatory response syndrome (SIRS).

A "cell activation/adhesion disorder" is a disorder characterized by the abnormal activation of cells, e.g., platelets and neutrophils, in the blood, and by the subsequent adhesion of these cells to each other or to activated cells in the surrounding vascular endothelium. Cell activation/adhesion disorders are a significant problem in a wide variety of medical pathologies. Endothelial cells, for example vascular, plural, pericardial or abdominal endothelial cells, can be activated by cytokines, e.g., interleukin-1 (IL-1), tumor necrosis factor-alpha (TNF-alpha) or bacterial endotoxins. In like manner, blood cells, particularly neutrophils and platelets, can be activated by agents such as GM-CSF, bacterial endotoxins, bacterial chemoattractants, TNF-alpha and the C5a component of complement. Activated cells have adhesion sites on their surfaces by which they can adhere to each other. Activated and adhered cells can form clumps, which can clog small blood vessels such as those found in the lungs and heart, and thereby reduce blood flow to surrounding tissue. The activated cells can also adhere to activated vascular endothelial cells; such adhesion can lead to subsequent degranulation of vascular endothelium, or to the release of mediators of cell damage such as superoxide anion ($O_2^-$) and proteolytic enzymes.

Amongst the cell activation/adhesion disorders to which the present invention is directed are reperfusion injuries, such as those related to the reperfusion of occluded blood vessels, or incidental to surgery in which blood flow is temporarily stopped (see, e.g., Seewaldt-Becker et al., "Effect of Anti-Adhesive Antibodies on Reperfusion Injury," (Springer et al., eds.) in: *Leukocyte Adhesion Molecules*, Springer-Verlag, New York (1990) pp. 138–148; and "Adhesion in Disease and Therapy," (Springer et al., eds.), in: *Leukocyte Adhesion Molecules*, Springer-Verlag, New York (1990), pp. 85–156). When there is a blockage in a blood vessel, surrounding endothelial cells, as well as downstream ischemic tissue, can be damaged. There can even be further damage to nearby endothelial cells when the occlusion is cleared. Such damaged cells can in turn induce activation in neutrophils and platelets after restoration of blood flow to the affected areas.

Prostaglandin treatment can reduce the damage exhibited in those animals afflicted with cell activation/adhesion disorders. The same cells which have receptors for activating agents can also have surface prostaglandin receptors. Without intending in any way to be limited by theory, it is believed that when prostaglandins bind to these prostaglandin receptors, they can deactivate the surface receptors responsible for the elevated levels of intercellular adhesion. The mechanism for this deactivation is believed to be a protein kinase A-mediated increase in intracellular cAMP levels.

An "anti-cell activation/adhesion effective amount" of a liposomal prostaglandin is any amount of the liposomal rostaglandin effective to ameliorate, inhibit or prevent the ctivation of adhesion sites on cells in the blood, or in surrounding vascular tissue, and/or the adhesion of such activated cells to other cells in the blood or surrounding vascular tissue. The anti-cell activation/adhesion amount will generally be effective to inhibit or lessen vascular occlusion resulting from such activation and intracellular adhesion.

Inflammation is a process of cytological and histological reactions occurring in affected blood vessels, and surrounding tissues, in response to an injury (see, e.g., *Stedman's Medical Dictionary (Illustrated)* (24th edition, J. V. Basmajian et al., eds.), Williams and Wilkins, Baltimore, Md. (1982), pp. 707–708). Inflammatory responses to such stimuli include local reactions and resulting morphological changes, destruction or removal of injurious materials and activation of repair mechanisms. Thus, inflammation can be part of the process by which animals heal themselves. However, inflammation can also occur in response to abnormal physiological stimuli and can cause problems in the body. Joints, for example, become inflamed in arthritic conditions such as gout, rheumatoid arthritis and Lyme disease (see, e.g., *Stedman's Medical Dictionary (Illustrated)*, supra at pages 123–124). These states may be characterized by the extravasation of cells, i.e, the egress of cells from the circulation into the inflamed area. Agents, such as prostaglandins, which can inhibit such extravasation, or which can otherwise inhibit inflammatory responses to abnormal physiological stimuli, can be used to ameliorate the inflammation.

An "anti-inflammatory disorder" effective amount" of the interdigitation-fusion liposomal arachidonic acid metabolite is any amount of the liposomal metabolite which is effective to ameliorate, inhibit or prevent inflammatory responses or reactions in animals afflicted with conditions characterized by abnormal inflammation, i.e., inflammation which is in response to abnormal physiological stimuli and which is not part of the body's normal repair processes in response to an injury.

Typically, the amount of the arachidonic acid metabolite administered to animals afflicted with cell activation and adhesion, inflammatory or toxemic disorders, and hence, the "anti-disorder effective" amount of the metabolite, is at least about $10^{-12}$ g of the metabolite per kg of body weight of the animal. Generally, the effective amount of the metabolite is from about $10^{-12}$ g of the metabolite per kg of body weight of the animal to about $10^{-3}$ g per kg of body weight. Preferably, the effective amount of the metabolite is from about $10^{-8}$ g of the metabolite per kg of body weight of the animal to about $10^{-4}$ g per kg of body weight. More preferably, the anti-cell activation and adhesion effective amount of the arachidonic acid metabolite is about $10^{-6}$ g of the metabolite per kg of body weight of the animal.

This invention is further described in the following Examples. However, those of ordinary skill in the art will readily determine that these examples are merely illustrative of the invention as defined in the claims which follow thereafter.

EXAMPLES

Example 1
Preparation of Interdigitation-Fusion Liposomes (IFVs)

A PGE$_1$ stock solution (1 mg/ml in ethanol) was prepared as follows: 20 mg of dried PGE$_1$ was transferred to a 20-ml vial, to which 20 ml of absolute ethanol was added. The PGE$_1$ was dissolved in the ethanol with gentle swirling; the resulting solution was stored at minus 20 degrees Celsius. PGE$_1$ was combined with an organic solvent solution of a saturated-acyl chain lipid (DPPC or DSPC) at a weight ratio (g/g) of PGE$_1$ to lipid of about 1:20. The PGE$_1$/lipid solution was used to prepare IFVs in accordance with the procedures disclosed in U.S. Ser. Nos. 07/961,277, 08/066,539 and 08/136,470, filed Oct. 14, 1992, May 24, 1993 and Oct. 13, 1993, respectively; the contents of these applications are incorporated herein by reference. Briefly, the PGE$_1$/saturated acyl chain lipid solution in an organic solvent was dried by evaporating off the organic solvent. The dried PGE$_1$/lipid mixture was rehydrated with an aqueous solution (50 mM citrate buffer or 50 mM acetate buffer) so as to form a suspension of multilamellar liposomes. These liposomes were then sized, and an inducer, for example, ethanol, was added to the sized liposomes. The liposome-inducer mixture was then incubated at a temperature below the transition temoerature (Tm) of the saturated-acyl chain lipid.

The percent of the PGE1 remaining in the DSPC IFVs and the DPPC IFVs following incubation in a pH 7 buffer was determined, and is given in FIG. 1 (see below).

What is claimed is:

1. A method of administering a prostaglandin to an animal which comprises administering to the animal a composition comprising a pharmaceutically acceptable carrier and an interdigitation-fusion liposome comprising said prostaglandin, a lipid bilayer comprising a lipid consisting essentially of a saturated acyl chain phosiphatidylcholine selected from the group consisting of dipalmitoyl phosphatidylcholine and distearoyl phosihatidylcholine and a compartment comprising a citric acid buffer, wherein at least about 60% of the metabolite is retained in the liposome after about 18 hours in an environment at about pH 7.

2. The method of claim 1, wherein said prostaglandin is prostaglandin E1.

3. The method of claim 1, wherein the animal is a human.

4. The method of claim 1, wherein the administration comprises intravenous administration.

5. The method of claim 1, wherein the animal is afflicted with a disorder characterized by cell activation and adhesion, inflammation or toxemia and wherein an amount of the composition comprising an anti-disorder effective amount of said prostaglandin is administered to the animal.

6. The method of claim 5, wherein the disorder is a vaso-occlusive disorder, an arthritic disorder or an autoimmune disorder.

7. The method of claim 5, wherein the disorder is selected from the group consisting of vasculitis, reperfusion injury, post-traumatic shock, myocardial infarction, rheumatoid arthritis, gout, systemic lupus erythematosus, juvenile diabetes, multiple sclerosis, Hashimoto's thyroiditis, septic shock, systemic inflammatory response syndrome, adult respiratory distress syndrome, post-operative complications, myasthenia gravis, burn injury and restenosis after angioplasty.

8. The method of claim 5, wherein the disorder comprises adult respiratory distress syndrome.

9. The method of claim 5, wherein the disorder comprises systemic inflammatory response syndrome.

10. The method of claim 5, wherein the anti-disorder effective amount of said prostaglandin is at least about $10^{-12}$ g of said prostaglandin per kg of body weight of the animal.

11. The method of claim 10, wherein the effective amount of said prostaglandin is from about $10^{-12}$ g of said prostaglandin per kg of body weight of the animal to about $10^{-3}$ g per kg of body weight.

12. The method of claim 11, wherein the effective amount of said prostaglandin is from about $10^{-8}$ g of said prostaglandin per kg of body weight of the animal to about $10^{-4}$ g per kg of body weight.

13. The method of claim 12, wherein the effective amount of said prostaglandin is about $10^{-6}$ g of said prostaglandin per kg of body weight of the animal.

14. The method of claim 1, comprising administering an additional bioactive agent to the animal, wherein the additional bioactive agent is selected from the group consisting of antiviral, antiarasitic, antifunagal, antibacterial, antimetabolic, antitelaucomic, anti-inflammators, antineonlastic, local anesthetic, bronchodilating, growth promoting, regenerative and diagnostic agents.

15. The method of claim 1, wherein the citric acid buffer has a pH of about 4.5.

16. The method of claim 1, wherein the liposome further comprises a drying protectant.

17. The method of claim 16, wherein the drying protectant is a sugar selected from the group consisting of lactose, maltose, sucrose, glucose, galactose, trehalose and raffinose.

18. The method of claim 1, wherein the interdigitation-fusion liposome comprises distearoyl phosphatidylcholine or dipalmitoyl phosphatidylcholine, prostaglandin E1 and a citric acid buffer having a pH of about 4.5, wherein an amount of the liposome comprising about $10^{-6}$ g of prostaglandin E1 per kg of the animal's body weight is administered intravenously and wherein the animal is afflicted with a cell activation and adhesion, inflammatory or toxemic disorder.

* * * * *